United States Patent [19]

Dormandy, Jr. et al.

[11] Patent Number: 4,741,730
[45] Date of Patent: May 3, 1988

[54] HYDROCEPHALUS SHUNT WITH IN-LINE FILTER

[75] Inventors: Ray H. Dormandy, Jr., Goleta, Calif.; Harold J. Hoffman, Toronto, Canada

[73] Assignee: American Hospital Supply, Evanston, Ill.

[21] Appl. No.: 432,502

[22] Filed: Oct. 4, 1982

[51] Int. Cl.⁴ ............................................. A61M 27/00
[52] U.S. Cl. ........................................... 604/8; 604/9; 604/128
[58] Field of Search ....................... 604/8–10, 604/126, 128–129, 185, 247; 210/130, 927

[56] References Cited

U.S. PATENT DOCUMENTS

| | | | |
|---|---|---|---|
| 926,197 | 6/1909 | Kim | 604/185 |
| 1,697,095 | 1/1929 | Turner | 210/130 X |
| 2,793,752 | 5/1957 | Jay | 210/130 |
| 3,452,757 | 7/1969 | Ames | 604/8 |
| 3,690,323 | 9/1972 | Wortman et al. | 604/8 |
| 3,756,243 | 9/1973 | Schulte | 604/185 X |
| 3,827,439 | 8/1974 | Schulte et al. | 604/9 |
| 3,985,140 | 10/1976 | Harris | 604/9 |
| 4,377,169 | 3/1983 | Banks | 604/8 |

*Primary Examiner*—Edward M. Coven
*Attorney, Agent, or Firm*—Roger A. Williams; Paul C. Flattery; Robert E. Hartenberger

[57] ABSTRACT

A shunt system for implantation in the body comprises a body having an inlet and an outlet and a first fluid-flow passageway extending between the inlet and outlet. A pressure regulated valve is provided within the first fluid-flow passageway to provide fluid flow at selected fluid pressures in the passageway. A filter is positioned within the first fluid-flow passageway. A second fluid-flow passageway extends between the inlet and outlet and provides a passageway through the body around the filter. A valve and valve seat is provided within the second fluid-flow passageway which can be selectively closed or opened to provide fluid flow through the second fluid-flow passageway.

24 Claims, 2 Drawing Sheets

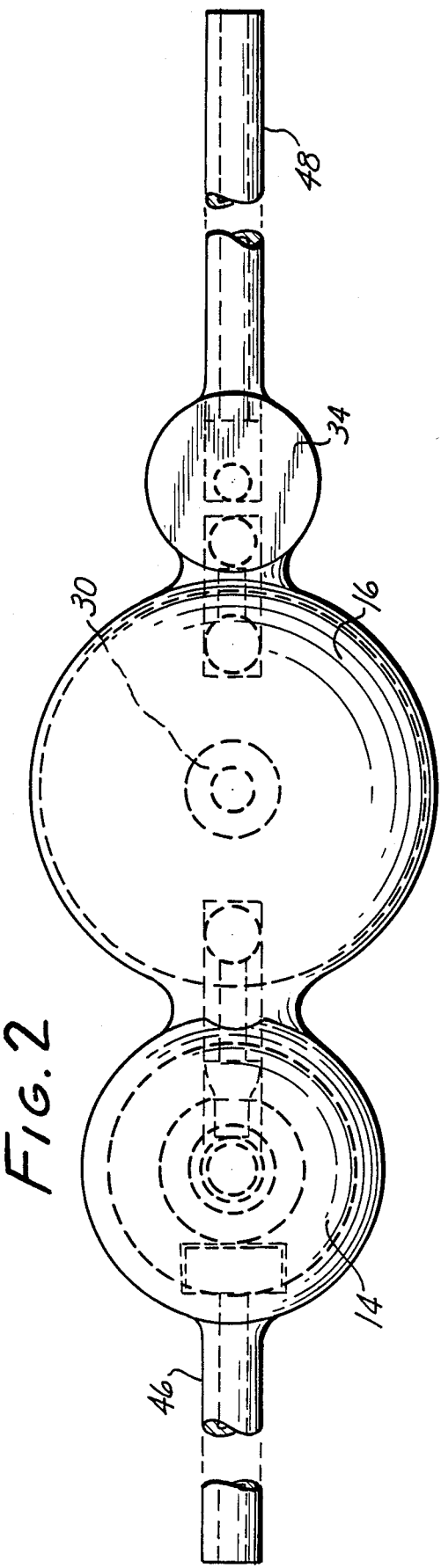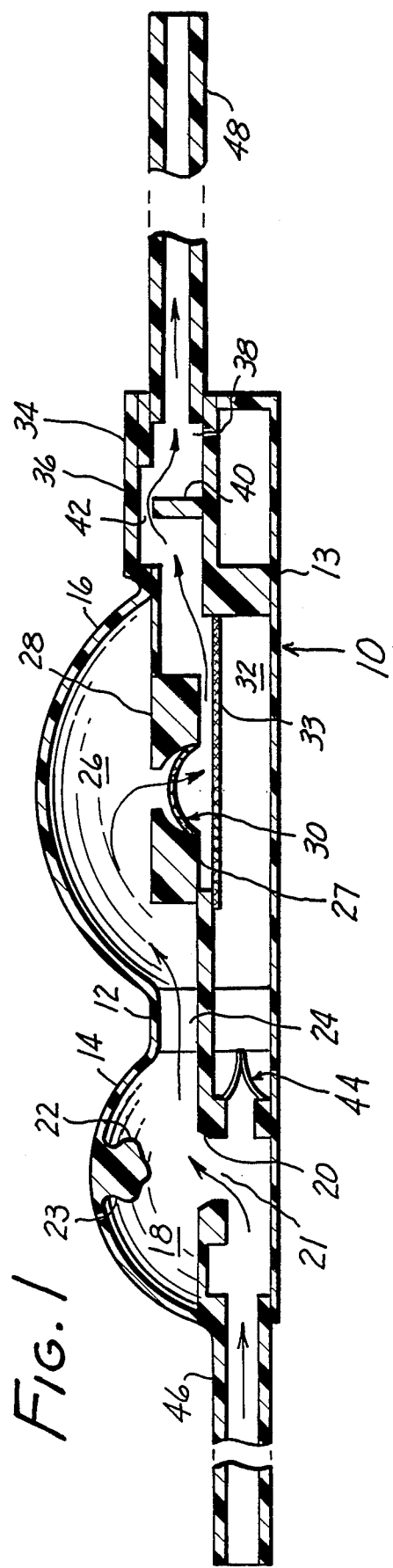

HYDROCEPHALUS SHUNT WITH IN-LINE FILTER

BACKGROUND OF THE INVENTION

The invention herein relates to a hydrocephalus shunt having an inline filter which is capable of being implanted in the body to provide for transfer of body fluids from one part of the body to any other part of the body.

Shunt systems for drainage of unwanted body fluids from one region of the body to another region are generally known. A well-known usage of such shunt systems is in the treatment of hydrocephalus, wherein excess cerebro-spinal fluid (CSF) is drained from the ventricles of the brain to either the right atrium or the peritoneal cavity. A known example of such a system is shown by Rudolph R. Schulte, U.S. Pat. No. 3,111,125, titled "Drainage Device." Another such device is disclosed by Allan J. Mishler in U.S. Pat. No. 3,595,240 and still another system is disclosed in U.S. Pat. No. 3,827,439 to Schulte and Portnoy.

The above-described devices are often implanted under the skin and connected to a ventricle drainage tube in the brain. The devices are also attached to a catheter which is inserted into the right atrium of the heart or into the peritoneum. After implantation and use over extended time periods, such devices tend to become clogged in certain individuals. Such clogging tends to occur at the catheter or passageway from the ventricle of the brain leading into inner chambers of the devices due to foreign materials which may be present in the CSF and which collects in the narrow, tubular passageways of the devices and at the openings in such passageways to the drain. Consequently, it is often necessary to perform second or subsequent operations on an individual to remove the devices which have become clogged.

Some of the devices provide means for flushing the devices. However, sometimes it is difficult to flush the devices or such flushing proves futile and incapable of removing the obstruction. In some instances, the devices can become obstructed with cells, which cells may be metastatic cancerous cells due to draining of tumors or cavities following operations for removal of tumors. In such instances, it is undesirable to permit such tumor cells to be transported to other parts of the body.

The inconvenience, cost and physical and psychological problems involved in performing the additional operations are considerable and undesirable. It would be desirable to provide a shunt or valve system which when obstructed can be manipulated to provide a by-pass around such an obstruction.

SUMMARY OF THE INVENTION

The invention herein is directed to an implantable shunt system having an in-line filter which is capable of shunting a fluid from one portion of the body to another portion of the body and filtering such fluid while it is being shunted. The shunt system herein can also provide a system for transferring cerebral spinal fluid from the ventricles of the brain to any other part of the body, such as the heart or peritoneal cavity.

The shunt system herein comprises a body having an inlet and an outlet. A first fluid-flow passageway extends through the body between the inlet and outlet. A pressure regulated valve is provided within the first fluid-flow passageway. The pressure regulated valve opens and provides fluid flow when a preselected fluid pressure is achieved in the passageway. A filter is positioned within the first fluid-flow passageway for filtering the fluid flowing therethrough. A second fluid-flow passageway also extends through the body between the inlet and outlet. The second fluid-flow passageway provides a fluid-flow passageway which extends around the filter in the first fluid-flow passageway. A valve is provided within the second fluid-flow passageway for selectively blocking or opening the passageway to fluid flow.

A pressure regulated valve can also be positioned within the second fluid-flow passageway. Such a second pressure regulated valve can also open upon experiencing a preselected fluid pressure within the fluid flowing through the shunt system.

BRIEF DESCRIPTION OF THE DRAWINGS

For a better understanding of the invention herein, reference can be made to the accompanying drawings wherein:

FIG. 1 is a side elevational view in cross section of the shunt system with in-line filter herein;

FIG. 2 is a top plan view of the shunt system of FIG. 1; and

DETAILED DESCRIPTION

Figure 3:
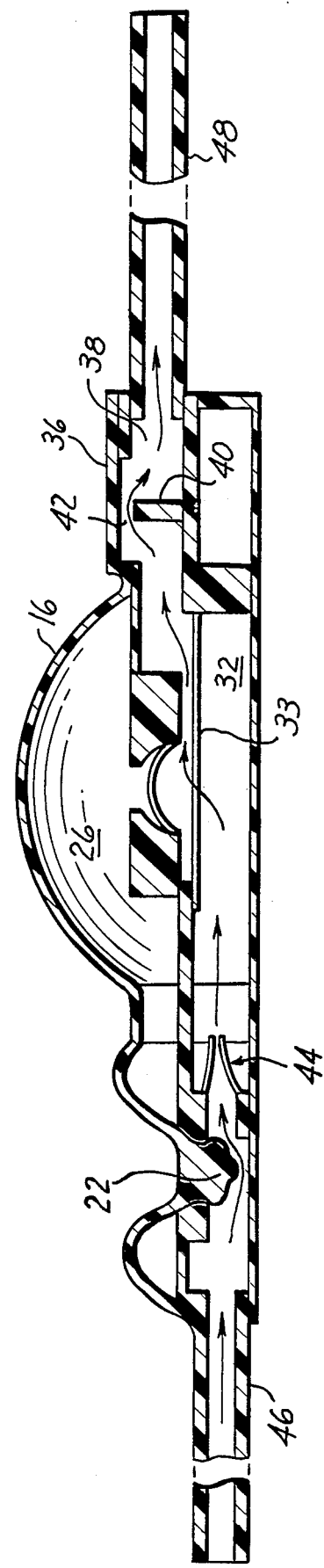
FIG. 3 is a side elevational view in cross section of the shunt system in the filtration mode of operation.

The shunt system herein will be described in relation to the drawings wherein FIG. 1 illustrates a working embodiment of the shunt system having an in-line filter for filtering the liquid being shunted. With regard to FIG. 1, the shunt 10 is disclosed. The shunt comprises a double-domed body 12 which is constructed of a resilient material, such as silicone rubber. The shunt has a relatively flat base 13. The base can have a reinforcing web or radiopaque web imbedded therein for facilitating location of the shunt when it is implanted. The base is preferably relatively flat so that it can be positioned against a portion of the skull of the patient in which the shunt is implanted.

The double-domed body 12 comprises a first dome 14 which forms a flexible wall on the body. A second dome 16 is formed by a resilient wall of the body. Both the first and second domes are resilient so as to be deformable when an external pressure is applied against the wall forming the domes.

The first domes defines a first chamber 18 within the shunt. Within the first chamber 18 is a valve seat 20 formed by a portion of the body of the shunt. A valve 22 or stopper is attached to the first dome and is positioned along the first dome such that when a pressure is exerted on the dome, the valve 22 seats within the valve seat 20, thereby precluding fluid flow through the passageway 21. The valve 22 and valve seat 20 cooperate to maintain the valve in a closed position. For example, the valve can have an annular recessed ring 23 which interlocks with the valve seat. The valve 22 can be closed by exerting an external force on the first dome. The valve 22 in a closed position for blocking the fluid-flow path 21 is shown in FIG. 3.

The second dome 16 forms within the body of the shunt a second chamber 26. The first and second chambers are interconnected through a fluid passageway or conduit 24.

Within the second chamber 26 is a valve seat 28 and a resilient diaphragm valve 30 seated in the valve seat. The valve seat is supported by the interior structure of the body of the shunt. The diaphragm valve can be selected so as to maintain a predetermined shunt pressure within the shunt. That is, the diaphragm valve 30 can be selected so that it opens to permit fluid flow only when a preselected fluid pressure is achieved in the second chamber 26. Preferably, the diaphragm valve is a one-way valve.

Also within the body of the shunt is a third chamber 32. The third chamber 32 is formed between the base 13 of the shunt and the interior wall 27 forming the bottom wall of the second chamber. The third chamber 32 has a filter 33 which extends between the third chamber and second chamber. The filter is a microporous filter, such as a spun microporous filter made of Teflon and polyvinylchloride. The filter can be of any filtration efficiency and for filtering CSF, it has been found that a 1.5 to 3 micron filter is preferable. The third chamber 32 is in fluid-flow communication with the inlet 46 of the shunt. Such fluid-flow communication is through a one-way valve 44 positioned between the inlet 46 and third chamber. Such a one-way valve can be a miter valve, as is shown in FIG. 1.

Positioned along the outlet path 48 for the fluid leaving the shunt is an occluder 34. The occluder 34 has a resilient wall 36 which can be deformed when external pressure is exerted upon it. The occluder 34 defines a fourth chamber 38 within the body of the shunt. Within the fourth chamber is an interior wall 40 positioned below the resilient wall 36 and spaced from the resilient wall by a restricted fluid-flow passageway 42. The interior wall 40 is spaced a distance from the resilient wall 36 such that when the resilient wall is deformed it contacts the interior wall, thereby occluding the fluid-flow pathway 42 between the resilient wall and interior wall.

The function of the shunt system herein will be described with regard to shunting CSF. Although it is to be understood that the shunt system can be used for implantation in the body for sampling CSF debris, for isolation of metastisized cancer cells, for treatment by radiation or drugs, or for forming an infusion cite upon implantation for drugs or agents for treatment, flushing or fluid sampling. The shunt system can be used for regulation and filtration of CSF shunting from any part of the central nervous system to any other body cavity. In general use, the shunt system herein is implanted under the skin near the skull. The inlet 46 of the shunt is connected to a drainage catheter, such as a ventricular drain. The outlet 48 can be connected to a drainage catheter leading either into the right atrium of the heart or the peritoneum.

When the shunt system herein is implanted, the valve 22 or stopper is positioned within the valve seat 20, thereby preventing fluid flow into the first chamber of the shunt system (FIG. 3). As the CSF flows into the inlet, it encounters the valve 22 obstructing fluid flow into the first chamber and therefore flows through the one-way 44 into the third chamber of the shunt. The one-way valve 44 can be selected so that it opens only when a preselected pressure in the CSF is achieved.

The flow of the CSF is then through the third chamber 32, through the filter 33, and into and through the fourth chamber 38 and outlet 48. Such a fluid-flow pathway is shown by the arrows in FIG. 3. The fluid-flow pathway as shown in FIG. 3 shows the normal operation of the shunt system. However, when the filter becomes occluded and fluid flow ceases or is inhibited through the shunt, then the shunt system herein provides a bypass around the occluded filter. The bypass can be manually actuated as will be later described. Such bypass capability can be effected readily without likelihood of serious damage due to occlusion of the filter and stoppage of fluid flow.

The bypass mode of operation is described again with regard to FIG. 1. The arrows in FIG. 1 show the fluid-flow pathway through the shunt system in such a bypass mode.

To place the shunt system in the bypass mode, external pressure is exerted on the resilient wall 36 of the occluder to occlude the fluid-flow pathway 42. When the fluid-flow pathway is occluded, then external pressure is exerted on the second dome 16 of the shunt system. Such pressures can be manually exerted on the shunt body. The pressure exerted within the body of the shunt by the externally exerted pressure on the second dome causes the valve 22 to unseat itself from the valve seat 20, opening passageway 21. When the passageway 21 is open, the CSF flows from the inlet 46 through the pathway 21 into the first chamber 18. The CSF flow is through pathway 21 due to the occlusion of the filter 33 and its inhibition of liquid flow therethrough. The CSF flows from the first chamber into and through the second chamber. If the pressure within the CSF is sufficient, it can open the diaphragm valve 30 within the second chamber and flows around the diaphragm valve. The CSF then flows into the fourth chamber and outwardly of the shunt through the outlet 48.

The shunt system herein has special utility in the treatment of surgically created hydrocephalus and hydrocephalus accompanied by brain tumors. For example, during many operations to remove brain tumors, much fluid is produced by the brain during and following the operation. In such situations, it is desirable to avoid any unwanted cancer cells which may be present in the fluid from being transported to other parts of the body. For this reason, an unfiltered hydrocephalus shunt which transports the excessive fluid output of the brain to other parts of the body is undesirable and the shunt system with in-line filter herein is especially desirable. That is, a shunt system having an in-line filter provides for filtration of any cancer cells which may be present in the fluid.

We claim:

1. A shunt system for implantation in the body comprising:

a body having an inlet and an outlet and a first fluid-flow passageway extending through the body between the inlet and outlet;

a pressure regulated valve means positioned within the first fluid-flow passageway for providing fluid flow therethrough at selected fluid pressures;

a filter positioned within the first fluid-flow passageway;

a second fluid-flow passageway extending between the inlet and outlet and providing a passageway through the body around the filter; and means within the second fluid-flow passageway for selectively blocking or opening the second fluid-flow passageway to fluid flow.

2. A shunt system as recited in claim 1 further comprising a pressure regulated valve means within the second fluid-flow passageway for providing fluid flow at selected fluid pressures.

3. A shunt system as recited in claim 2 wherein the pressure regulated valve means in the second fluid-flow passageway comprises a one-way valve.

4. A shunt system as recited in claim 2 wherein the pressure regulated valve means in the second fluid-flow passageway comprises a diaphragm valve.

5. A shunt system as recited in claim 1 wherein the pressure regulated valve means positioned within the first fluid-flow passageway comprises a one-way valve.

6. A shunt system as recited in claim 5 wherein the one-way valve comprises a miter valve.

7. A shunt system as recited in claim 1 wherein the blocking or opening means within the second fluid-flow passageway comprises a valve and valve seat.

8. A shunt system as recited in claim 7 further comprising actuating means within the body for actuating the selective blocking or opening means to provide fluid flow or prevent fluid flow through the second fluid-flow passageway.

9. A shunt system as recited in claim 8 wherein the actuating means comprises a restricted fluid-flow passageway within the outlet and a resilient wall on at least a portion of the body whereby external pressure exerted on the resilient wall portion of the body causes deformation of the resilient wall to occlude the restricted fluid-flow passageway and a pressure responsive body portion which upon application of external pressure concomitantly with occluding the restricted fluid-flow passageway opens the blocking or opening means within the second fluid-flow passageway.

10. A shunt system as recited in claim 1 wherein the filter comprises about a 1.5 to 3 micron microporous filter.

11. A shunt system as recited in claim 1 wherein the body is comprised of silicone.

12. A shunt system for implantation in the body comprising:
a double-domed resilient body having an inlet and an outlet and a first fluid-flow passageway extending through the body between the inlet and outlet and a first chamber formed by the first dome and a second chamber formed by the second dome;
a pressure regulated valve means positioned within the first fluid-flow passageway for providing fluid flow therethrough at selected fluid pressures;
a filter positioned within the first fluid-flow passageway;
a second fluid-flow passageway extending through the body between the inlet and outlet and providing a fluid-flow passageway through the first and second chambers around the filter; and
means with the second fluid-flow passageway for selectively blocking or opening the second fluid-flow passageway to fluid flow.

13. A shunt system as recited in claim 12 further comprising a pressure regulated valve means within the second fluid-flow passageway for providing fluid flow at selected fluid pressures.

14. A shunt system as recited in claim 13 wherein the pressure regulated valve means in the second fluid-flow passageway comprises a one-way diaphragm valve.

15. A shunt system as recited in claim 12 wherein the pressure regulated valve means positioned within the first fluid-flow passageway comprises a one-way valve.

16. A shunt system as recited in claim 12 wherein the blocking or opening means within the second fluid-flow passageway comprises a valve and valve seat positioned between the inlet and first chamber.

17. A shunt system as recited in claim 16 wherein the valve is attached to the first dome.

18. A shunt system as recited in claim 12 further comprising actuating means within the body of the shunt for actuating the selective blocking or opening means to provide fluid flow through the second fluid-flow passageway.

19. A shunt system as recited in claim 18 wherein the actuating means comprises a restricted fluid-flow passageway within the outlet and a resilient wall on at least a portion of the body whereby external pressure exerted on the resilient wall portion of the body causes deformation of the resilient wall to occlude the restricted fluid-flow passageway and a pressure responsive body portion on the second dome which upon application of external pressure concomitantly with occluding the restricted fluid-flow passageway opens the blocking or opening means within the second fluid-flow passageway.

20. A shunt system as recited in claim 12 wherein the body comprises silicone.

21. A shunt system as recited in claim 12 wherein the filter comprises a microporous filter of about 1.5 to 3 microns.

22. A shunt system for implantation in the body comprising:
a body having an inlet and outlet and at least two fluid-flow passages extending therethrough;
pressure regulated valve means within each of the fluid-flow passages which provide fluid flow at selected fluid pressures in the passages;
a filter positioned within the first fluid-flow passageway; and means within the second fluid-flow passageway for selectively blocking or opening the second fluid-flow passageway to fluid flow.

23. A shunt system for implantation in the body comprising:
a body having an inlet and outlet and at least two fluid-flow passages extending therethrough;
pressure regulated valve means within each of the fluid-flow passages which provide fluid flow at selected fluid pressures in the passages;
a filter positioned within the first fluid-flow passageway; and
a valve and valve seat within the second fluid-flow passageway which can be selectively opened or closed to permit or prevent fluid flow through such second fluid-flow passageway.

24. A shunt system as recited in claim 23 further comprising actuating means within the body to open the valve in the second fluid-flow passageway.

* * * * *